United States Patent
Mikkola

Patent Number: 5,834,074
Date of Patent: Nov. 10, 1998

[54] PRESERVATION OF DRIED FLOWERS

[76] Inventor: Frederick P. Mikkola, 729 Carr, Lakewood, Colo. 80215

[21] Appl. No.: 752,804
[22] Filed: Nov. 20, 1996
[51] Int. Cl.$^6$ .................................................. A01N 3/00
[52] U.S. Cl. ................... 428/24; 47/DIG. 11; 106/162.1; 427/4; 504/114
[58] Field of Search ........................... 427/4, 421; 71/26; 127/29, 30, 32; 47/DIG. 11; 426/106, 103; 504/114; 106/162.1

[56] References Cited

U.S. PATENT DOCUMENTS

| | | | |
|---|---|---|---|
| 3,842,539 | 10/1974 | Sacalis ........................................ | 47/58 |
| 3,929,448 | 12/1975 | Brantley ...................................... | 71/68 |
| 4,375,465 | 3/1983 | Drakoff ..................................... | 514/553 |
| 5,298,478 | 3/1994 | Yamamoto et al. ...................... | 504/115 |
| 5,364,643 | 11/1994 | Morimoto et al. ...................... | 426/102 |
| 5,368,873 | 11/1994 | Aebi et al. ............................... | 426/310 |
| 5,420,015 | 5/1995 | Wruech .................................... | 106/162 |
| 5,421,121 | 6/1995 | Bestwick et al. ....................... | 47/41.01 |
| 5,547,693 | 8/1996 | Krochta et al. .......................... | 426/90 |
| 5,580,840 | 12/1996 | Harms et al. ............................ | 504/115 |

Primary Examiner—Diana Dudash
Attorney, Agent, or Firm—Litman, McMahon & Brown, LLC

[57] ABSTRACT

A process for preserving dried flowers includes hanging flowers and floral greens by their stems, spraying them with a preservative solution in a relatively cool atmosphere, leaving them in the cool atmosphere for a selected length of time, and drying the sprayed flowers and greens in a relatively warm atmosphere. The preservative solution is a water solution of a common detergent at a concentration of about 0.25 to 1.0 per cent by weight and corn syrup at a concentration of about 20 to 33 per cent by weight.

13 Claims, 1 Drawing Sheet

PRESERVATION OF DRIED FLOWERS

BACKGROUND OF THE INVENTION

Cut flowers and arrangements of cut flowers are often given as gifts or to express sentiments. Flowers are also used as decorations in homes, on dining tables, in churches, in commercial settings, and the like. Fresh, live cut flowers are generally preferred because of their appearance and scents. Certain types of flowers are used as seasonal decorations which may last a week or more. Toward the end of such a period, the appearance of such seasonal flowers may deteriorate as blooms droop, leaves wilt, and petals drop off the blooms.

There has been an increased interest in the use of dried flowers for purposes similar to the use of freshly cut flowers. Problems with flowers which are simply dried include the fading of colors of the blooms and leaves during drying and the fact that parts of the flower become brittle. Conventionally dried flowers are so delicate that mere handling to form arrangements often damages such flowers. Packaging and storing of conventionally dried flowers, as by florists, also results in considerable damage to such products.

There have been attempts to preserve dried flowers using certain chemicals to decrease their brittleness. Such preservatives are usually applied "stemically", that is, by allowing the flowers to draw a solution of the preservative through the stems of the flowers as the flowers are dried. Known processes for preserving dried flowers often cause fading of the colors of the blooms, leaves, and stems. To compensate for such loss of color, the treated flowers are often bleached and dyed in an attempt to restore the expected colors. Flowers so processed often do not appear natural. Additionally, some such preservative chemicals impart an unpleasant odor to flowers so processed. Finally, many flowers preserved conventionally have an excessive flexibility such that the stems and other parts of the preserved flowers tend to droop. This creates problems in assembling arrangements since such flowers must often be supported by wires or other structures to maintain their desired positions within the arrangements.

SUMMARY OF THE INVENTION

The present invention provides an improved process for preserving cut flowers and floral greens, an improved preservative solution, and floral products preserved by the improved process.

In general, the preservation process includes applying a water solution of common detergent and sugar to the floral elements and allowing them to dry. A preferred preservative solution is formed by an unscented, granular laundry detergent at a concentration of from 0.25 to 1.0 per cent by weight, corn syrup at a concentration of from 20 to 33 per cent by weight, and the remainder water. The preservative solution may be applied by dipping cut flowers and floral greens or, preferably, by spraying it onto such floral elements.

The cut flowers and greens are hung up by their stems and sprayed in a relatively cool atmosphere, preferably in a range of from 45 to 55 degrees Fahrenheit. The sprayed elements are left in the cool atmosphere for about four hours and allowed to drain any excess preservative solution. Thereafter, the drained floral elements are placed in a relatively warm atmosphere with an ambient temperature in a range of 85 to 95 degrees Fahrenheit, in which drying of any remaining solution and the floral elements occurs.

The flowers and floral greens, thus processed, retain their natural colors and textures. Embrittlement of stems, leaves, and blooms is avoided. The preserved floral elements may then be assembled into arrangements or may be packaged for storage or for shipment with minimal damage to the products. The floral elements preserved according to the present invention have an indefinite storage life, as far as is known, and a long life in use on display.

OBJECTS AND ADVANTAGES OF THE INVENTION

The principal objects of the present invention are: to provide an improved process for preserving floral elements such as flowers and floral greens; to provide such a process including applying a preservative solution of a detergent and a sugar prior to drying; to provide such a process in which the preservative solution is sprayed onto the floral elements; to provide such a process in which the floral elements are sprayed with the preservative solution in a relatively cool atmosphere, drained and left in the cool atmosphere for a selected length of time, and dried in a relatively warm atmosphere for a selected length of time; to provide such a process in which the preserved floral elements retain natural colors, textures, and scents; to provide such a process which prevents embrittlement of the floral elements whereby they can be packaged and shipped with minimal damage thereto; to provide a preservative solution for such a process which includes a water solution of an unscented, granular laundry detergent at a concentration of 0.25 to 1.0 per cent by weight and corn syrup at a concentration of 20 to 33 per cent by weight; to provide such a preservative which has minimal environmental impact as far as toxicity and other hazards are concerned; to provide preserved floral elements as products of such a process; and to provide such a process for preserving floral elements, a preservative solution, and preserved floral products which are economical to practice and produce, which result in a superior product, and which are particularly well adapted for their intended purpose.

Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

DETAILED DESCRIPTION OF THE INVENTION

Figure 1:
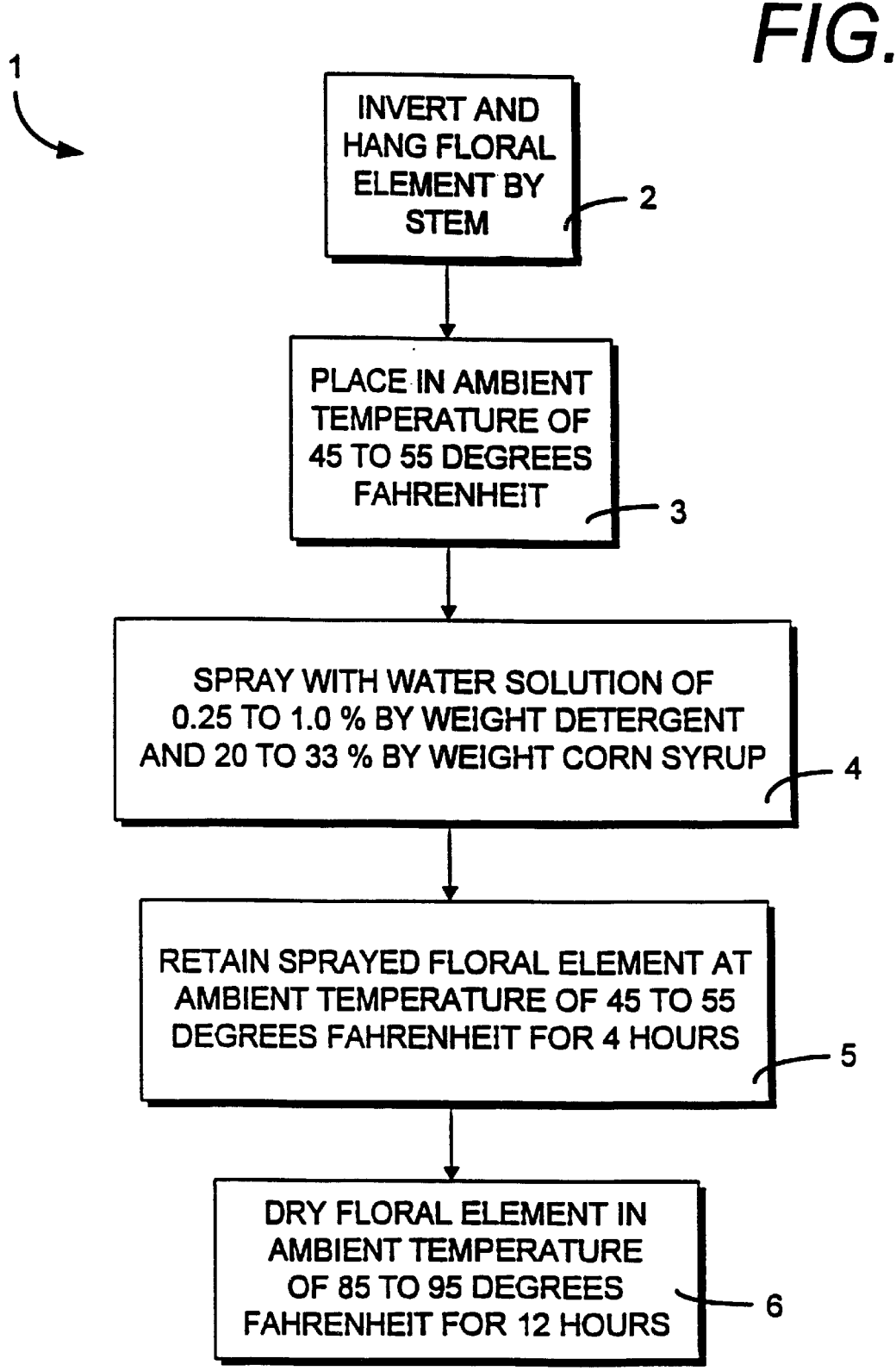
FIG. 1 is a flow diagram illustrating an improved process for preserving cut floral elements which embodies the present invention.

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Referring to the drawings in more detail:

The reference numeral 1 generally designates a process for preserving floral elements which embodies the present invention. In general, the process 1 includes the step of spraying a floral element with a preservative solution which includes a detergent and a sugar and allowing the floral element to dry with the preservative solution thereon. In the present invention, the term "floral elements" is used to generically refer to various types of cut flowers as well as floral greens, such as fronds, leaves, ferns, and the like which may be used to in flower arrangements, for example, to fill out such arrangements.

The preservative solution is a water solution of the detergent and the sugar. A preferred detergent in the present invention is unscented, granular laundry detergent at a concentration of about 0.25 to 0.5 per cent by weight of the total solution. Alternatively, other types of detergents can be used; however, it is preferred that the detergent does not impart an objectional odor or an artificial scent to the treated floral element. The preferred sugar component is corn syrup at a concentration of about 20 per cent by weight of the total solution. Other sugar products can alternatively be employed in the present invention, such as maple syrups, honeys, and dissolved granular sugar. Preferably, the sugar component employed does not have a noticeable scent, which may rule out the use of a maple syrup in some concentrations. Corn syrup is preferred because it is low in scent and is relatively inexpensive compared to maple syrup or honey.

The concentration percentages given above are for the final preservative which is used to spray the floral elements. The preservative solution may be provided at a stronger concentration for storage purpose to minimize bulk. For use, it can be diluted to the desired concentration. A suggested concentration for storage purposes is about 1.0 per cent by weight for the detergent and about 33 per cent by weight for the corn syrup.

In practice of the process 1, fresh cut flowers and greens are separated and hung up in an invented orientation by their stems at process step 2 (FIG. 1). The suspended floral elements are placed in a relatively cool atmosphere with an ambient temperature of from about 45 to 55 degrees Fahrenheit at step 3. The preservative solution can be applied by dipping; however, the solution is preferably sprayed on at step 4. Spraying can be done using manually actuated spray bottles or by a mechanized sprayer system using a pump. Light spray pressure is desired to avoid damaging the flowers and greens. All surfaces of the floral elements are substantially covered by the solution, although drenching is not required. The detergent component of the solution is believed to function as a surfactant to spread the sugar component fairly evenly on the surfaces of the floral elements.

After spraying, the floral elements are left hanging in the cool atmosphere for about four hours at step 5 of the process 1. Draining of excess preservative solution occurs during this period and, possibly, some absorption of the preservative solution by the floral elements. At the end of the four hours, the drained floral elements are moved to a relatively warm atmosphere having an ambient temperature of from about 85 to 95 degrees Fahrenheit and left there for about twelve hours at step 6 of the process 1. During this period, drying of any remaining preservative solution occurs in addition to all parts of the flowers and greens.

Floral elements treated according to the process 1 retain their natural colors in stems, leaves, petals, and the like and retain a more natural texture than either drying without preservatives or drying with conventional preservatives. Plant fibers which connect leaves and petals retain their strength and flexibility such that the floral elements tend to stay intact during handling. Thus, the floral elements treated by the process 1 can be handled for assembling arrangements or packaging with minimal damage to the flowers and greens. The packaged floral elements may also be packed in cases for shipping or for storage and later use with minimal damage. The packaged floral elements have been found to have a long shelf life, particularly if sealed in evacuated packages. Additionally, the floral elements treated by the process 1 have a long life in use when exposed to air, humidity, and the like.

The use of the process 1 has further advantages of having low environmental impact since the components of the preservative solution are common household products which are neither flammable nor highly toxic.

It is to be understood that while certain forms of the present invention have been illustrated and described herein, it is not to be limited to the specific forms or arrangement of parts described and shown.

What is claimed and desired to be secured by letters patent is as follows:

1. A process for preserving a cut floral element and comprising the steps of:
    (a) applying to substantially the entirety of a substantially fresh floral element a water solution of a detergent and a sugar, said solution including:
        (1) a deterrent at a concentration in a range of 0.25 to 1.0 per cent by weight;
        (2) a sugar based syrup at a concentration in a range of 20 to 33 per cent by weight; and
        (3) a remaining percentage of water; and
    (b) drying said floral element with said preservative solution thereon.

2. A process as set forth in claim 1 wherein said applying step includes the step of:
    (a) spraying said preservative solution to apply same to said floral element.

3. A process as set forth in claim 1 and including the steps of:
    (a) suspending said floral element in an inverted orientation; and
    (b) spraying said preservative solution to apply same to said floral element.

4. A process as set forth in claim 1 and including the steps of:
    (a) applying said preservative solution to said floral element in an ambient temperature in a range of approximately 45 to 55 degrees Fahrenheit;
    (b) retaining said floral element at said ambient temperature in a range of approximately 45 to 55 degrees Fahrenheit for approximately four hours; and
    (c) thereafter drying said floral element at an ambient temperature in a range of approximately 85 to 95 degrees Fahrenheit.

5. A process as set forth in claim 4 and including the step of:
    (a) retaining said floral element at said ambient temperature in a range of approximately 85 to 95 degrees Fahrenheit for approximately twelve hours.

6. A process as set forth in claim 1 and including the steps of:
    (a) reapplying said preservative solution to said floral element; and
    (b) further drying said floral element with said solution thereon.

7. A process for preserving a cut floral element and comprising the steps of:
   (a) suspending a substantially fresh floral element by a stem of said element in an inverted orientation;
   (b) spraying a preservative solution onto substantially the entirety of the suspended floral element, said solution including:
      (1) a detergent at a concentration in a range of 0.25 to 1.0 per cent by weight;
      (2) a sugar based syrup at a concentration in a range of 20 to 33 per cent by weight; and
      (3) a remaining percentage of water;
   (c) spraying said preservative solution on said floral element at an ambient temperature in a range of approximately 45 to 55 degrees Fahrenheit;
   (d) retaining said floral element at said ambient temperature in a range of approximately 45 to 55 degrees Fahrenheit for approximately four hours; and
   (e) thereafter drying said floral element with said preservative solution thereon at an ambient temperature in a range of approximately 85 to 95 degrees Fahrenheit for approximately twelve hours.

8. A process as set forth in claim 7 and including the steps of:
   (a) reapplying said preservative solution to said floral element; and
   (b) further drying said floral element with said solution thereon.

9. A floral element preservative solution comprising:
   (a) an unscented, granular laundry detergent having a concentration in a range of 0.25 to 1.0 percent by weight;
   (b) a sugar based syrup having a concentration in a range of 20 to 33 per cent by weight; and
   (c) a remaining percentage of water.

10. A solution as set forth in claim 9 wherein:
    (a) said syrup includes a corn syrup.

11. A solution as set forth in claim 9 wherein:
    (a) said syrup includes a honey.

12. A solution as set forth in claim 9 wherein:
    (a) said syrup includes a maple syrup.

13. A dried floral product comprising:
    (a) a floral element;
    (b) a coating applied to substantially the entirety of said floral element prior to drying said floral element as a water solution of a detergent and a sugar; and
    (c) said solution including:
       (1) an unscented, granular laundry detergent having a concentration in a range of 0.25 to 1.0 per cent by weight;
       (2) corn syrup having a concentration in a range of 20 to 33 per cent by weight; and
       (3) a remaining percentage of water.

* * * * *